US012779083B2

(12) United States Patent
Park et al.

(10) Patent No.: US 12,779,083 B2
(45) Date of Patent: Nov. 3, 2026

(54) NERVE SUTURE PATCH HAVING SELF-HEALING PROPERTY AND PRODUCTION METHOD THEREOF

(71) Applicants: KOREA UNIVERSITY RESEARCH AND BUSINESS FOUNDATION, Seoul (KR); RESEARCH & BUSINESS FOUNDATION SUNGKYUNKWAN UNIVERSITY, Gyeonggi-do (KR)

(72) Inventors: Jong Woong Park, Seoul (KR); Donghee Son, Gyeonggi-do (KR); Mikyung Shin, Seoul (KR)

(73) Assignees: KOREA UNIVERSITY RESEARCH AND BUSINESS FOUNDATION, Seoul (KR); RESEARCH & BUSINESS FOUNDATION SUNGKYUNKWAN UNIVERSITY, Gyeonggi-do (KR)

( * ) Notice: Subject to any disclaimer, the term of this patent is extended or adjusted under 35 U.S.C. 154(b) by 954 days.

(21) Appl. No.: 17/792,617

(22) PCT Filed: Dec. 7, 2020

(86) PCT No.: PCT/KR2020/017747

§ 371 (c)(1),
(2) Date: Jul. 13, 2022

(87) PCT Pub. No.: WO2021/149911

PCT Pub. Date: Jul. 29, 2021

(65) Prior Publication Data

US 2023/0058182 A1 Feb. 23, 2023

(30) Foreign Application Priority Data

Jan. 23, 2020 (KR) ........................ 10-2020-0009337
Dec. 4, 2020 (KR) ........................ 10-2020-0168213

(51) Int. Cl.
*A61L 17/10* (2006.01)
*A61L 17/00* (2006.01)

(52) U.S. Cl.
CPC ............. *A61L 17/10* (2013.01); *A61L 17/005* (2013.01); *A61L 2300/414* (2013.01); *A61L 2420/02* (2013.01); *A61L 2430/32* (2013.01)

(58) Field of Classification Search
CPC ............................. A61L 2430/32; A61L 17/10
See application file for complete search history.

(56) References Cited

U.S. PATENT DOCUMENTS

| | | | | |
|---|---|---|---|---|
| 2003/0069639 A1 | | 4/2003 | Sander et al. | |
| 2004/0049187 A1 | * | 3/2004 | Burnett | A61B 18/18 606/52 |
| 2008/0125870 A1 | | 5/2008 | Carmichael et al. | |

FOREIGN PATENT DOCUMENTS

| | | | | |
|---|---|---|---|---|
| CN | 102772823 | | 11/2012 | |
| CN | 110240712 | | 9/2019 | |
| CN | 110448727 | | 11/2019 | |
| KR | 10-0718073 | | 5/2007 | |
| KR | 10-2011-0110667 | | 10/2011 | |
| KR | 10-2019-0143298 | | 12/2019 | |
| KR | 20190143298 | | 12/2019 | |
| KR | 20190143298 A | * | 12/2019 | B32B 3/10 |
| WO | WO2015134589 A1 | * | 9/2015 | C12N 15/00 |

OTHER PUBLICATIONS

Tao Chen et al, Ultra tough, Self-Healing, and Tissue-Adhesive Hydrogel for Wound Dressing, ACS Applied Materials & Interfaces 2018 10 (39), 33523-33531, DOI: 10.1021/acsami.8b10064 (Year: 2018).*
Jiheong Kang et al, Tough and Water-Insensitive Self-Healing Elastomer for Robust Electronic Skin, Adv. Mater. 2018, 30, 1706846 (Year: 2018).*
Asja Pettignano et al, Boronic acid-modified alginate enables direct formation of injectable, self-healing and multistimuli-responsive hydrogels, Chem. Commun., 2017,53, 3350-3353 (Year: 2017).*
Kr20190143298a, Korean Intellectual Property Office English Translation document, downloaded in Feb. 2025 (Year: 2025).*
Laura Stephenson Carter, An Interview with Hynda Kleinman, Alumni News, Intramural Research Program, The Matrigel-Maker's Story, National Institutes of Health, Office of the Director, vol. 21, Issue 4, Jul.-Aug. 2013 (Year: 2013).*
Skorb et al., "Layer-by-Layer approaches for formation of smart self-healing materials," Polym. Chem., 2013,4,4834 (Year: 2013).*
Talebian, S. et al. Self-Healing Hydrogels: The Next Paradigm Shift in Tissue Engineering?. Advanced Science. 2019, vol. 6, article No. 1801664, inner pp. 1-47.
Hong, S. H. et al. Dynamic Bonds between Boronic Acid and Alginate: Hydrogels with Stretchable, Self-healing, Stimuli-responsive, Re-moldable, and Adhesive Properties. Biomacromolecules. Mar. 30, 2018, pp. 1-30.
Kang, J. et al. Tough and Water-Insensitive Self-Healing Elastomer for Robust Electronic Skin. Advanced Materials. 2018, vol. 30, article No. 1706846, inner pp. 1-8, Supporting Information p. 1-22.
International Search Report, Application No. PCT/KR2020/017747, dated Apr. 8, 2021, 3 pages.
Hong, Sang Hyeon et al. Alginate-Boronic Acid: pH-Triggered Bioinspired Glue for Hydrogel Assembly, Advanced Functional Materials, vol. 30, Issue 26 on Dec. 13, 2019, 9 pages.

(Continued)

*Primary Examiner* — Robert A Wax
(74) *Attorney, Agent, or Firm* — Casimir Jones, S.C.; Robert A. Goetz

(57) ABSTRACT

The present invention relates to a nerve suture patch having a self-healing property, and a production method thereof, and more specifically, to a self-healing nerve suture patch containing a self-healing polymer and a hydrogel, and a production method thereof. The nerve suture patch may be rapidly attached to epineurium by the adhesiveness of the hydrogel and easily suture a damaged nerve.

5 Claims, 5 Drawing Sheets

(56) References Cited

OTHER PUBLICATIONS

Jiang, Chenyu et al., Self-healing polyurethane-elastomer with mechanical tunability for multiple biomedical applications in vivo, Nature Communication, 12:4395, Jul. 20, 2021, 13 pages.
Zhang, EnMian et al., Novel self-healing hydrogels and their applications in tissue engineering, Science China Press, Feb. 21, 2019, 49, 3, 250-265, English Abstract.

* cited by examiner

0 Seconds

20 Seconds

70 Seconds

NERVE SUTURE PATCH HAVING SELF-HEALING PROPERTY AND PRODUCTION METHOD THEREOF

TECHNICAL FIELD

The following description relates to a nerve suture patch having self-healing ability and a method for preparing the same, and more particularly, to a nerve suture patch having self-healing ability capable of chemical bonding with an epineurium and a method for preparing the same.

BACKGROUND ART

Peripheral nerve damage causes serious impairment in social life. Peripheral nerve injury accounts for 2.8% of trauma patients. For example, there are 360,000 severely paralyzed patients each year in the United States, resulting in 8,648,000 patients with limited daily activities, of which 4,916,000 are bedridden. Peripheral nerve procedures are also very common, with 300,000 patients undergoing the procedure each year in Europe and 200,000 patients undergoing the procedure each year in the United States.

A peripheral nerve conduit is a connector that guides nerve regeneration by connecting severed peripheral nerves or central nerves. Nerves in limbs that have been cut by accidents or surgery are difficult to connect unless the cut site is tightly sutured.

However, if the cut surfaces are separated by 5 mm or more, direct suturing is not possible, and there is no method other than autologous nerve transplantation. However, autograft has disadvantages in that it is necessary to use one's own nerves, and there is a limit to the number of nerves that can be harvested.

Severed nerves have the property of growing at a rate of about 1 mm per day in the peripheral part, so if a tube-type nerve conduit is introduced into the cut site using this property, the severed nerve can be regenerated.

The nerve conduit serves as a pathway to connect the damaged nerve tissue and regenerate nerve fibers. If the nerve conduit is used, it uses the principle that when both ends of a severed nerve are connected to this conduit, nerve fibers grow from one side of the nerve within the conduit to regenerate the nerve.

The first successful use of nerve conduits was in 1990 by Lundborg using silicone tubes. However, since silicone is difficult to decompose due to the nature of the silicone, there is a cumbersome operation to remove the tube after the nerve is completely restored. In addition, non-absorbable silicone conduits do not have porosity around the conduits. Thus, nutrients do not pass through them, so nerve regeneration is difficult. There is a drawback that the speed is slow even if the nerves are regenerated Meanwhile, for the purpose of applying to a longer defect area, a nerve conduit was developed in Japan in which the same biodegradable polymer is used as a base material, the inner side is filled with a collagen sponge with excellent tissue affinity, and the outer side is coated with a collagen solution several times. As a result of animal experiments, it was confirmed that complete restoration was achieved in the peripheral nerve area that had been damaged by about 8 cm, and it has been applied to clinical practice since 2002.

However, in the case of these nerve conduits, due to the nature of PLA used as a base material, they lack flexibility. Therefore, there is a problem in which if the physical properties are not strengthened using a reinforcing material, it is difficult to secure the original inner diameter and maintain the shape until complete nerve tissue restoration due to frequent muscle movements after implantation, and it also crumbles when sutured with the cut nerve at the same time.

Meanwhile, the conventional nerve conduit is manufactured by injecting a conduit-forming material into a conduit mold having a certain shape or by smearing a conduit-forming material around the conduit mold to prepare a conduit, and then inserting a fiber into the conduit. Since this conventional manufacturing method uses a conduit mold, there are disadvantages in which it is necessary to go through the manufacturing process of the conduit mold, and the size of the nerve conduit cannot be manufactured below a certain level according to the conduit mold, and it is also necessary to go through a step of removing the conduit mold.

In addition, since the modulus of the conventional nerve conduit is different from the modulus of the peripheral nerve, the nerve compression was very severe. In this case, there may be a problem in which the oxygen supply through the blood vessels in the peripheral nerves is insufficient, causing nerve necrosis.

Therefore, there is a need to develop a nerve suture technology that can solve the problems of the conventional nerve conduit.

PRIOR ART DOCUMENT

Korean Patent No. 10-0718073

DISCLOSURE OF THE INVENTION

Technical Goals

In order to solve the above problems, an aspect provides a nerve suture patch having excellent elasticity and self-healing ability capable of chemical bonding with peripheral nerves and a method for preparing the same.

Technical Solutions

In order to achieve the above object, according to an aspect, there is provided a self-healing nerve suture patch including a self-healing polymer and a hydrogel patch, in which the hydrogel patch includes at least one selected from the group consisting of alginate, polyacrylamide (PAA), polyetherimide (PEI), polyethylene glycol (PEG), polyethylene oxide (PEO), polyhydroxyethyl methacrylate (PHEMA), polyvinyl alcohol (PVA), poly(N-isopropylacrylamide) (PNIPAM), polyvinylpyrrolidone (PVP), polylactic acid (PLA), polyglycolic acid (PGA), polycaprolactone (PCL), gelatin, collagen, carrageenan, hydroxyalkylcellulose, alkylcellulose, silicone, rubber, agar, carboxyvinyl copolymer, polydioxolane, polyacryl acetate, polyvinyl chloride, fibrin, matrigel, gelatin methacrylate (GelMA), maleic anhydride/vinyl ether, chitosan, and boronic acid.

As an embodiment of the present invention, the hydrogel patch is characterized in that it includes alginate and boronic acid.

As another embodiment of the present invention, the hydrogel patch is characterized in that it includes a conjugated polymer in which boronic acid is conjugated to alginate.

As still another embodiment of the present invention, the hydrogel patch is characterized in that it further includes a nerve growth factor.

As still another embodiment of the present invention, the self-healing polymer is characterized in that it includes: a first moiety including a polymer backbone selected from the group consisting of polydimethylsiloxane (PDMS), polyethylene oxide (PEO), perfluoropolyether (PFPE), polybutylene (PB), poly(ethylene-co-1-butylene), poly(butadiene), hydrogenated poly(butadiene), polybutylene and poly(ethylene oxide)-poly(propylene oxide) block copolymer or random copolymer and poly(hydroxyalkanoate) and 4,4'-methylenebis(phenylurea) (MPU); and a second moiety including isophorone bisurea (IU).

As still another embodiment of the present invention, the self-healing polymer is characterized in that it has a Young's modulus of 1 to 3000 kPa, and an elongation of 1200 to 3000%.

In addition, according to another aspect, there is provided a method for preparing a self-healing nerve suture patch, the method including steps of:

(S1) preparing a self-healing polymer film by applying a self-healing polymer on a substrate and drying the same;

(S2) treating the surface of the film with plasma; and (S3) laminating a hydrogel on the surface of the plasma-treated film.

Advantageous Effects

The self-healing polymer has excellent stress relieving properties, so when it is applied to a peripheral nerve, there is almost no nerve compression. The hydrogel applied together has a mechanical modulus similar to that of a peripheral nerve, so that shear force and compression can be minimized.

BEST MODE FOR CARRYING OUT THE INVENTION

Figure 1:
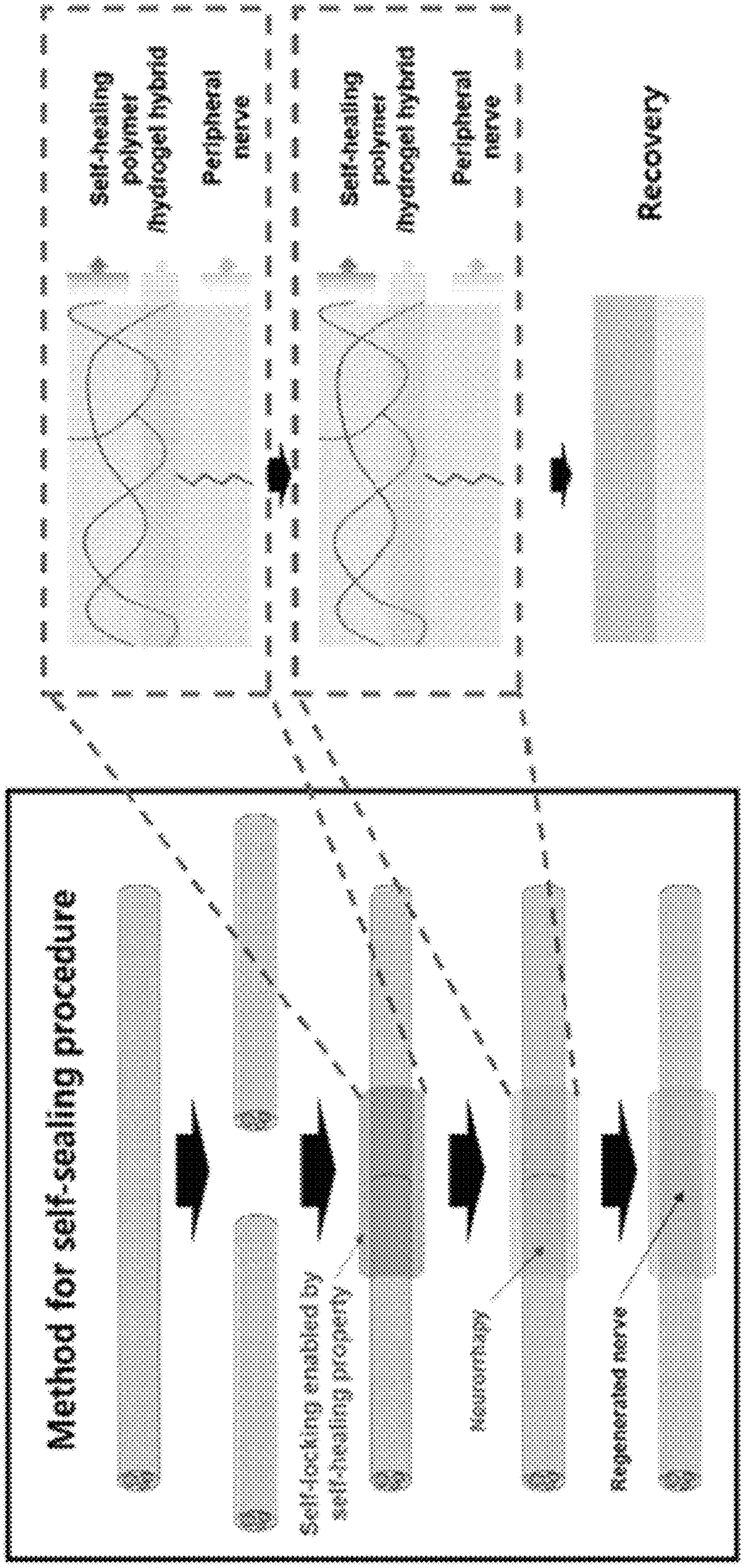
FIG. 1 is a view schematically showing when the hydrogel patch and the self-healing polymer film in the present invention are applied to peripheral nerves.

The present invention can have various changes and can have various example embodiments, so specific example embodiments are illustrated in the drawings and described in detail in the detailed description.

However, this is not intended to limit the present invention to specific embodiments, it should be understood to include all modifications, equivalents and substitutes included in the spirit and technical scope of the present invention. In describing the present invention, if it is determined that a detailed description of a related known technology may obscure the gist of the present invention, the detailed description thereof will be excluded.

The terms used in the present application are only used to describe specific example embodiments and are not intended to limit the present invention. The singular expression includes the plural expression unless the context clearly dictates otherwise.

In the present invention, it is to be understood that terms such as "comprising" or "having" are intended to designate that the features, numbers, steps, operations, components, parts, or combinations thereof described in the specification exist, and this does not preclude the presence or addition possibility of one or more other features, numbers, steps, operations, components, parts, or combinations thereof.

The present invention relates to a nerve suture patch having self-healing ability, and more particularly, to a nerve suture patch having self-healing ability capable of chemical bonding with an epineurium.

In one example embodiment of the present invention, there is provided the self-healing nerve suture patch which is characterized in that it includes a self-healing polymer and a hydrogel patch, and the hydrogel patch includes at least one selected from the group consisting of alginate, polyacrylamide (PAA), polyetherimide (PEI), polyethylene glycol (PEG), polyethylene oxide (PEO), polyhydroxyethyl methacrylate (PHEMA), polyvinyl alcohol (PVA), poly(N-isopropylacrylamide) (PNIPAM), polyvinylpyrrolidone (PVP), polylactic acid (PLA), polyglycolic acid (PGA), polycaprolactone (PCL), gelatin, collagen, carrageenan, hydroxyalkylcellulose, alkylcellulose, silicone, rubber, agar, carboxyvinyl copolymer, polydioxolane, polyacryl acetate, polyvinyl chloride, fibrin, matrigel, gelatin methacrylate (GelMA), maleic anhydride/vinyl ether, chitosan, and boronic acid.

Prior to the description, among the terms used in the present invention, the term "self-healing polymer" may refer to a polymer that recognizes a damaged or scratched area by itself and restores it to a previous state. In particular, in one example embodiment of the present invention, the combination of the dynamic stress relaxation characteristics of the self-healing polymer and the low modulus of the hydrogel has advantages in preventing nerve necrosis due to nerve compression and facilitating nerve regeneration.

FIG. 1 is a view schematically showing a process of i applying a self-healing nerve suture patch of the present invention into peripheral nerves.

Referring to FIG. 1, the self-healing nerve suture patch according to an example embodiment of the present invention includes a self-healing polymer and a hydrogel patch. Specifically, a hydrogel patch may be included on one side of the self-healing polymer film, and when the self-healing nerve suture patch is applied to the epineurium, the hydrogel patch may be attached to the epineurium.

In a specific embodiment, the hydrogel patch may include at least one selected from the group consisting of alginate, polyacrylamide (PAA), polyetherimide (PEI), polyethylene glycol (PEG), polyethylene oxide (PEO), polyhydroxyethyl methacrylate (PHEMA), polyvinyl alcohol (PVA), poly(N-isopropylacrylamide) (PNIPAM), polyvinylpyrrolidone (PVP), polylactic acid (PLA), polyglycolic acid (PGA), polycaprolactone (PCL), gelatin, collagen, carrageenan, hydroxyalkylcellulose, alkylcellulose, silicone, rubber, agar, carboxyvinyl copolymer, polydioxolane, polyacryl acetate, polyvinyl chloride, fibrin, matrigel, gelatin methacrylate (GelMA), maleic anhydride/vinyl ether, chitosan, and boronic acid. For example, the hydrogel patch includes alginate and boronic acid and may include a conjugated polymer in which boronic acid is conjugated to alginate.

In addition, the hydrogel patch according to an example embodiment of the present invention may further include a nerve growth factor (NGF, neurotrophic factor), and the nerve growth factor may facilitate nerve regeneration during nerve suturing.

The hydrogel patch is manufactured by combining a gel-forming agent and a crosslinking agent, and a transdermally absorbable formulation having a patch form is designed to fundamentally solve the problem of conventional skin irritation, the toxicity due to residual solvent and/or unreacted monomer, and crosslinking for a long time.

Moreover, the self-healing polymer may include: a first moiety including a polymer backbone selected from the group consisting of polydimethylsiloxane (PDMS), polyethylene oxide (PEO), perfluoropolyether (PFPE), polybutylene (PB), poly(ethylene-co-1-butylene), poly(butadiene), hydrogenated poly(butadiene), polybutylene and poly(ethylene oxide)-poly(propylene oxide) block copolymer or random copolymer and poly(hydroxyalkanoate) and 4,4'-methylenebis(phenylurea) (MPU); and a second moiety including isophorone bisurea (IU). Thus, the self-healing polymer may have a Young's modulus of 1 to 3000 kPa, and an elongation of 1200% to 3000%. The self-healing polymer of the present invention has the same Young's modulus and elongation as described above, so it has a modulus similar to that of a peripheral nerve. Accordingly, when wrapped around and in contact with a damaged nerve, shear force and compression can be minimized More specifically, the self-healing polymer may be a PDMS-$MPU_x$-$IU_{1-x}$ polymer represented by Chemical Formula 1 below. Meanwhile, x may be in the range of 0.3 to 0.6.

As described above, unlike the conventional nerve conduit having a different modulus from that of a peripheral nerve to generate nerve compression, the present invention uses a patch containing a self-healing polymer having excellent stress relaxation characteristics to relieve nerve compression and grafts a hydrogel having a mechanical modulus of 10 to 99 kPa to the self-healing polymer to provide a nerve suture patch kit having a similar modulus to that of the peripheral nerve, thereby removing the nerve compression.

Accordingly, the present invention can provide a method for nerve splice using the above-described kit for nerve suturing, and the method for nerve splicing surgery may include the following steps:

(1) covering both cuts of the cut nerve with the self-healing nerve suture patch and contacting them;

(2) leaving them after the contact; and (3) removing the nerve suture patch.

In addition, the present invention may provide a method for preparing a self-healing nerve suture patch, the method including steps of:

(S1) preparing a self-healing polymer film by applying a self-healing polymer on a substrate and drying the same;

(S2) treating the surface of the film with plasma; and (S3) laminating a hydrogel on the surface of the plasma-treated film.

The plasma treatment is oxygen plasma treatment. By treatment with plasma, the surface of the self-healing polymer is modified to be hydrophilic so that the hydrogel can be easily laminated.

[Chemical Formula 1]

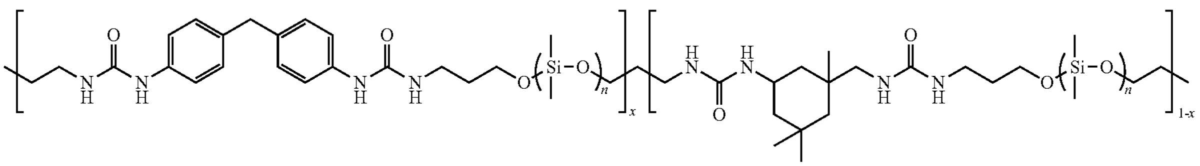

Furthermore, the alginate-boronic acid conjugate polymer is applied to the polymer film made of the self-healing polymer to prepare a self-healing nerve suture patch. 10% of the total polymer chain of the alginate may be substituted with boronic acid, and through this, it has adhesiveness and can be easily attached to the nerve.

As described above, the nerve suture patch includes a self-healing polymer and an adhesive polymer film, and the adhesive polymer film includes a polysaccharide material such as alginate.

As described above, the patch in which the polysaccharide material is thinly coated on the self-healing polymer can be applied to the nerve part. Through this, the patch of the present invention can easily suture the severed nerve.

In addition, the nerve suture patch may further include nerve growth factor (NGF) in the alginate-boronic acid conjugated polymer.

Hereinafter, the present invention will be described with reference to the following examples. However, the examples are for describing the present invention in detail, and the scope of the present invention is not limited to the following examples.

EXAMPLE

Example 1. Preparation of Nerve Suture Patch Having Self-Healing Ability

1-1. Preparation of Polymer Films

A self-healing polymer film was prepared by using a polymer of PDMS-$MPU_x$-$IU_{1-x}$ of the following formula (1).

[Chemical Formula 1]

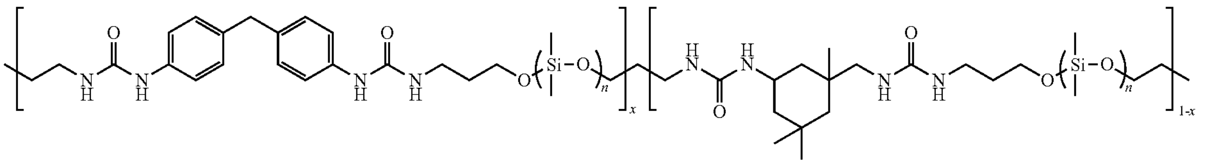

A PDMS-$MPU_{0.4}$-$IU_{0.6}$ film was prepared. Specifically, 4 g of PDMS-$MPU_{0.4}$-$IU_{0.6}$ in $CHCl_3$ was stirred at 50° C. for 3 hours and then cooled at room temperature. Then, the solution was poured onto an OTS-treated silicon substrate (e.g., 4 inches), dried at room temperature for 6 hours, and then dried at about 80° C. under reduced pressure (about 100 torrs) for 3 hours.

Accordingly, a self-healing polymer film was prepared. The polymer film had a thickness of 0.5 mm. Then, the film was cut to a size of 1 cm×1 cm.

The surface of the prepared self-healing polymer film was treated with oxygen plasma to modify the surface of the self-healing polymer film to be hydrophilic. Then, an adhesive polymer was synthesized for lamination on the surface of the self-healing polymer film.

1-2. Alginate-Boronic Acid Production Method 1 g of alginate polymer was dissolved in 250 mL of 0.1 M MES buffer (pH 4.5). 700 mg of 1-(3-dimethylaminopropyl)-3-ethylcarbodiimide hydrochloride and 100 mg of N-hydroxysuccinimide were dissolved in 10 mL of tertiary distilled water, and the mixture was added to the alginate solution. Thereafter, 3-aminophenylboronic acid hydrochloride (300 mg) was dissolved in 10 mL of tertiary distilled water, and the mixture was added to the above solution. After 12 hours of reaction, dialysis was performed for 3 days. A dried polymer was obtained through freeze-drying. In addition, a nerve growth factor was added to the solution and mixed.

1-3. Preparation of Nerve Suture Patches

The alginate-boronic acid conjugate was thinly coated on the self-healing polymer film prepared above in the same manner.

Figure 2A:
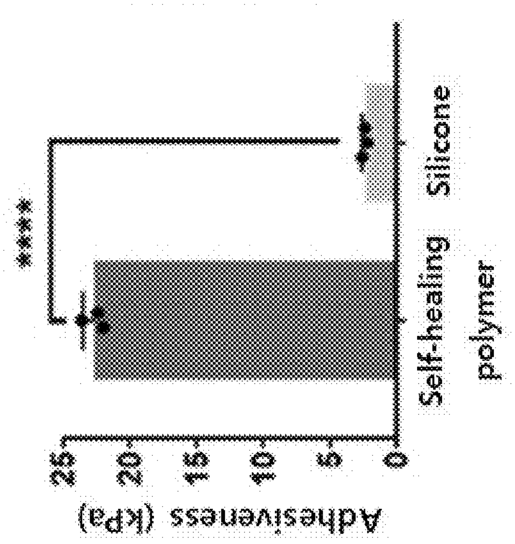
FIG. 2 is a view showing the results of confirming the adhesive strength and physical properties of the nerve suture patch having self-healing ability according to an example embodiment of the present invention.

Example 2. Adhesion and Physical Properties of Nerve Suture Patch 2-1. Measurement of Adhesion of Nerve Suture Patches Nerves have strong flexibility and elasticity, so physical activity causes stress, requiring a modulus that distributes the force applied to the surgical site. Since the self-healing polymer of this nerve suture patch has flexible properties similar to that of nerve tissue, it can show the effect of improving adhesion by dispersing the stress applied to the tissue and the attached part. In order to prove the contents, through a universal test machine, a self-healing polymer-based nerve suture patch and a general silicone (PDMS)-based suture patch were prepared in the same manner as in Example 1, and they were prepared in a size of 0.5 cm in width and 1 cm in length. A polyethylene terephthalate (PET) film (backing film) was attached to the back side of the film and the tissue without the adhesive polymer. Then, the tissue and the adhesive patch were attached, and the sample was measured while stretched upwards at a rate of 20 mm per minute using a 10 N load cell. All experiments were measured three or more times, and the suture patch using a self-healing polymer improved the adhesive force more than 10 times than the silicone-based suture patch as shown in FIG. 2A.

2-2. Measurement of Physical Properties of Nerve Suture Patches

Figure 2B:
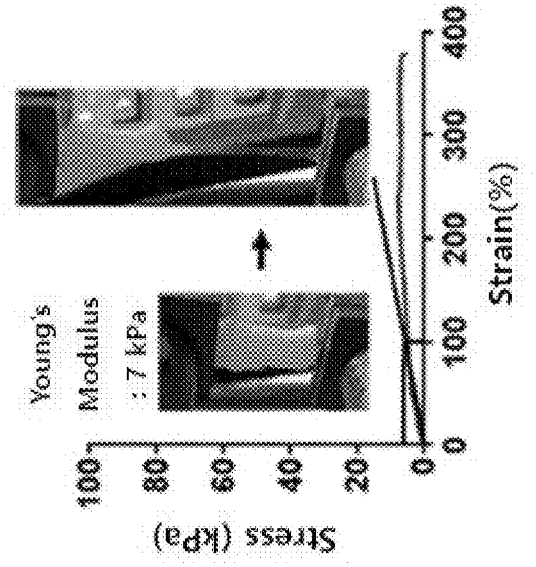

This nerve suture patch wraps around nerves to help nerve regeneration. Therefore, elasticity of the patch generated by nerve contraction and tension is required, and additional compression should not adversely affect nerve regeneration. Conventional polymers such as PDMS have the potential to cause nerve damage due to these properties, but the self-healing polymer used in this patch dramatically reduces this compression over time. In order to measure the corresponding physical properties, the self-healing polymer of this patch was installed with a width of 5 mm and a length of 10 mm in a universal test machine and tensioned at a rate of 20 mm/min. As the polymer stretched, the force applied to the equipment increased. When the force reached 0.3 N, the tension of the polymer was stopped. Then, the stress of the polymer was analyzed over time. As shown in FIG. 2B, it was confirmed that the polymer stress was 7 kPa.

Figure 2C:
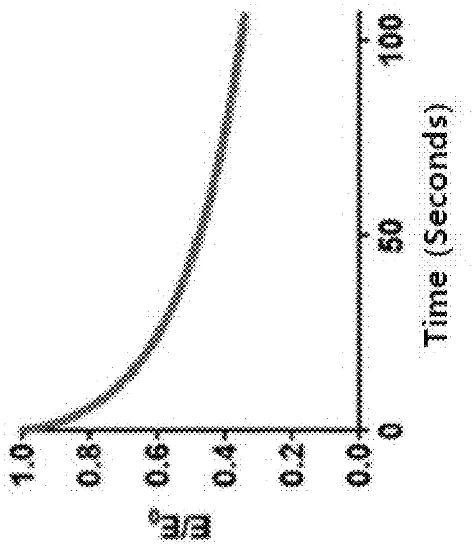

The stress relaxation effect of the polymer over time was confirmed by dividing the stress over time by the stress (0.3 N) applied to the initial polymer. As shown in FIG. 2C, it was confirmed that the force applied to the initial polymer was reduced to half compared to the initial within 1 minute and continued to decrease thereafter. These properties minimize nerve compression when applied to nerves, thereby preventing nerve necrosis and helping regeneration.

EXPERIMENTAL EXAMPLE

Figure 3A:
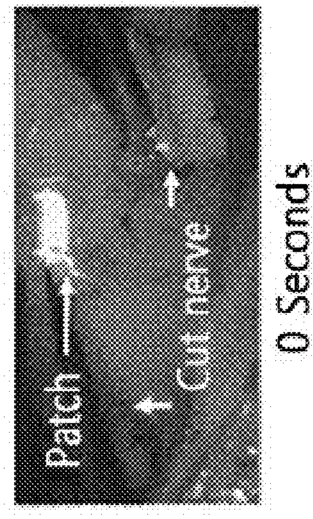
FIG. 3 is a view showing the results of confirming that the nerve is sutured by introducing a nerve suture patch having self-healing ability according to an example embodiment of the present invention into a cut nerve.

Experimental Example 1. Animal Preparation and Implantation of Nerve Suture Patch All animal experiments were performed and processed in accordance with the regulations of the Korea Institute of Science and Technology Institutional Animal Care and Use Committee (Approval No. 2018-067). Experimental procedures were performed according to the Guide for the Care and Use of Laboratory Animals. For implantation of the nerve suture patch, Sprague-Dawley rats (male, 300 g) were anesthetized using Zoletil and Xylize cocktail (3:1 mg/kg) by intraperitoneal injection. After a deep level of anesthesia was carried out, a skin incision was extended to the dorsal side of the paw in order to expose the hind paw muscles. The femoral-biceps and semitendinosus muscles were identified, and the sciatic nerve was exposed from the muscle, and then the nerve was cut (FIG. 3A).

Figure 3B:
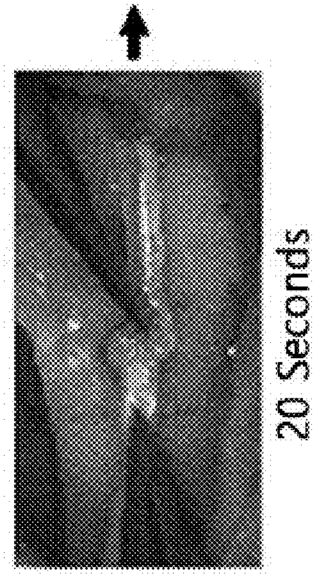
Figure 3C:
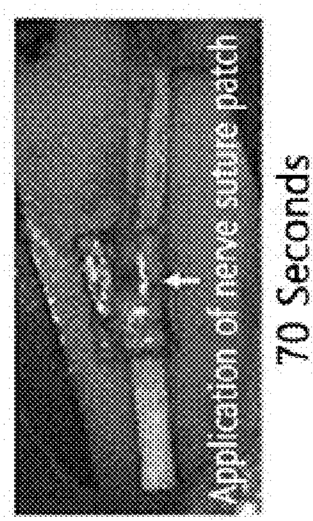

As shown in FIGS. 3B and 3C, surgery was operated in which both cut nerves were placed in the middle of the film and then were winded with the nerve suture patch prepared in Example 1. Comparing the time required at this time, as shown in FIG. 3F, it was about 70 seconds, which can save more than 10 times compared to the operation time using the existing suture thread.

Figure 3D:
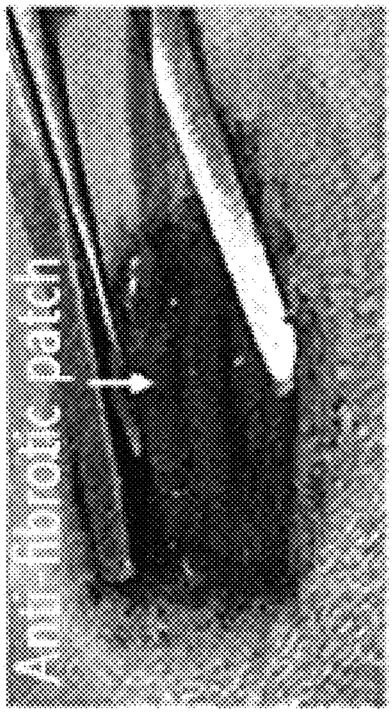
Figure 3E:
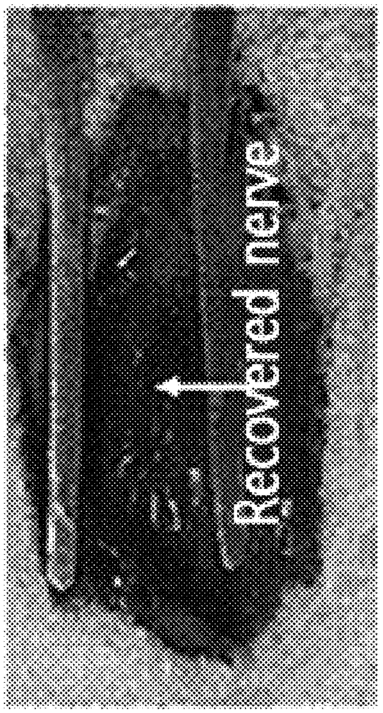
Figure 3F:
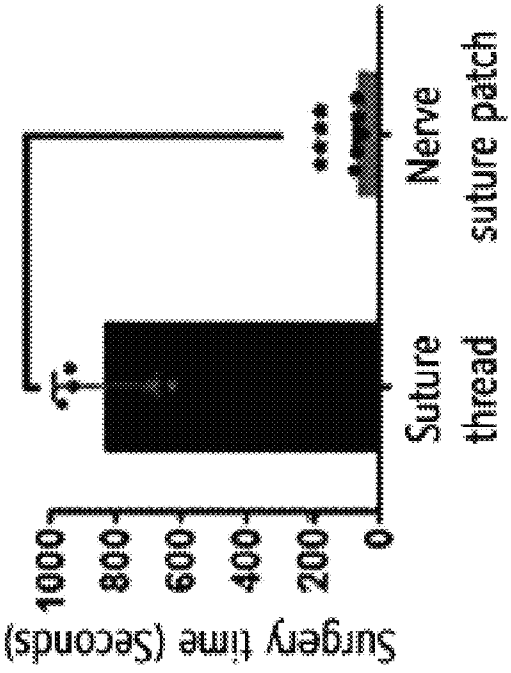

As shown in FIGS. 3D and 3E, when the patch was opened 10 days after nerve surgery, it was observed that fibrosis did not progress around the nerve and the cut nerve was recovered. To determine the degree of recovery after surgery, the sciatic functional index (SFI) evaluation method and the myelin sheath thickness (g-ratio, axon diameter/total fiber diameter, normal range: 0.6-0.8) measurement method were used.

Figure 3G:
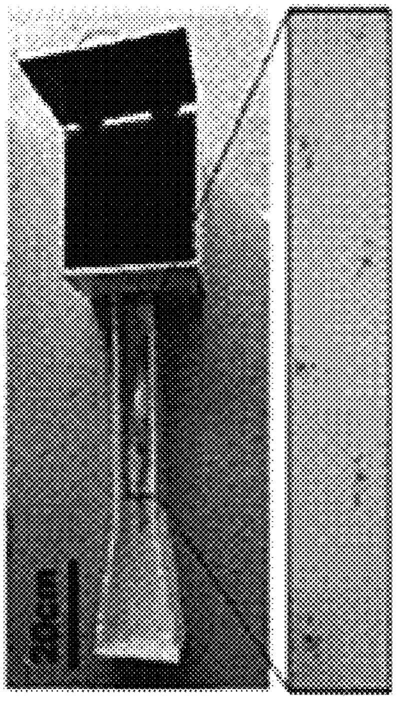
Figure 3H:
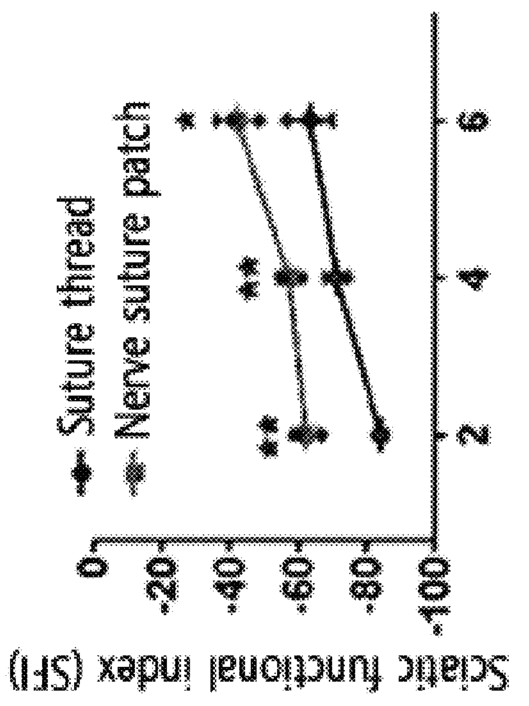
Figure 3I:
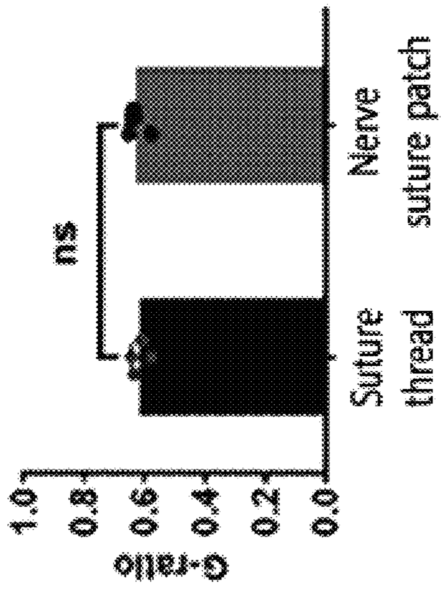

FIG. 3G shows the experimental design for measuring the sciatic nerve index. The front and back paws of the mouse were stained with black ink, and the mouse was lured into a black box. The sciatic nerve index level was measured based on the footprints taken. The sciatic nerve index could be obtained by substituting the total plantar length (PL), the distance between the first to fifth toes (TS), and the distance between the second and fourth toes and the middle toes (IT) into the formula. It was expressed on a scale from −100 without neural function to 0 with normal function. As shown in FIG. 3H, it was confirmed that the functional recovery of the nerve was further improved by the nerve suture patch compared to the suture thread. In addition, the recovery rate according to nerve conductance could be measured by obtaining the ratio of the total outer diameter to the inner axon diameter during nerve recovery through the thickness of myelin (G-ratio). As shown in FIG. 3I, the normal range was 0.6 to 0.8, and the same recovery rate was observed as the suture thread after 12 weeks.

The above results confirmed that the nerve suture patch of the present invention has an excellent recovery effect on a cut nerve.

In the above, a specific portion of the present invention has been described in detail, and it is clear for those of ordinary skill in the art that this specific description is only a preferred example embodiment, and the scope of the present invention is not limited thereto. Accordingly, the substantial scope of the present invention is defined by the appended claims and their equivalents.

The invention claimed is:

1. A self-healing nerve suture patch comprising a self-healing polymer film, wherein the self-healing polymer comprises a first moiety including a polymer backbone of polydimethylsiloxane (PDMS) and 4,4'-methylenebis(phenylurea) (MPU) and a second moiety including isophorone bisurea (IU), and is represented by PDMS-MPUx-IU1-x wherein x is in the range of 0.3 to 0.6, and wherein the self-healing polymer has a Young's modulus of 1 to 3000 kPa, and a hydrogel layer disposed on at least one surface of the self-healing polymer film, the surface having been treated with oxygen plasma;

wherein the hydrogel layer comprises a conjugated polymer in which boronic acid is conjugated to alginate.

2. The self-healing nerve suture patch of claim 1, wherein the hydrogel layer further includes a nerve growth factor.

3. The self-healing nerve suture patch of claim 1, wherein the self-healing polymer film has an elongation of 1200% to 3000%.

4. A method for preparing a self-healing nerve suture patch, the method comprising steps of:

(S1) preparing a self-healing polymer film by applying a self-healing polymer on a substrate and drying the self-healing polymer, wherein the self-healing polymer comprises a first moiety including a polymer backbone of polydimethylsiloxane (PDMS) and 4,4'-methylenebis(phenylurea) (MPU) and a second moiety including isophorone bisurea (IU), and is represented by PDMS-MPUx-IU1-x wherein x is in the range of 0.3 to 0.6, and wherein the self-healing polymer has a Young's modulus of 1 to 3000 kPa;

(S2) treating a surface of the self-healing polymer film with oxygen plasma; and (S3) laminating a hydrogel layer comprising a conjugated polymer in which boronic acid is conjugated to alginate on the plasma-treated surface of the self-healing polymer film.

5. The method for preparing a self-healing nerve suture patch of claim 4, wherein the hydrogel layer further includes a nerve growth factor.

* * * * *